United States Patent [19]

Simon et al.

[11] Patent Number: 5,434,077
[45] Date of Patent: Jul. 18, 1995

[54] BORRELIA BURGDORFERI STRAIN 257

[75] Inventors: Markus M. Simon; Ulrich E. Schaible; Klaus Eichmann, all of Freiburg; Michael Kramer; Wallich Reinhard, both of Heidelberg, all of Germany

[73] Assignees: Max-Planck-Gesellschaft zur Förderung der Wissenschaften e.V., Göttingen; Deutsches Krebsforschungszentrum Stiftung des Öffentlichen Rechts, Heildelberg, both of Germany

[21] Appl. No.: 68,063

[22] Filed: May 27, 1993

Related U.S. Application Data

[62] Division of Ser. No. 937,054, Aug. 26, 1992, abandoned, which is a division of Ser. No. 585,310, Sep. 19, 1990, Pat. No. 5,178,859.

[30] Foreign Application Priority Data

Sep. 19, 1989 [DE] Germany .......................... 39 31 236.4
May 17, 1990 [DE] Germany .......................... 40 15 911.6

[51] Int. Cl.⁶ .......................... C12N 1/00; C12N 1/20; A61K 39/02
[52] U.S. Cl. .................................. 435/243; 424/93.1; 424/234.1
[58] Field of Search ...................... 435/252, 243, 69.3, 435/245, 93 R, 93.1

[56] References Cited

FOREIGN PATENT DOCUMENTS 0492964 7/1992 European Pat. Off. ...... C12N 15/31
WO9004411 5/1990 WIPO .......................... A61K 39/02
WO9200055 1/1992 WIPO .......................... C12N 15/31

(List continued on next page.)

OTHER PUBLICATIONS

Schaible et al J. Exp Med. 170: 1427–1432 1989.
Barbour et al Inf & Imm 1984 vol. 45: 94–100.
Wallich et al Nucleic Acids Research, Cloning & Frequency of the Gene Encoding the Outer Surface Protein A(OdpA) of a European *Borrelia burgdorferi* Isolate 17:8864 1989.
Kramer et al Immunobiol 181:357–366 1990.
Schwan et al Journ. of Clini Microbiol. 26:893–895 1988.
Johnson et al., "Experimental Infection of the Hamster with *Borrelia burgdorferi*", Annals of the New York Academy of Sciences, p. 258, 1987.
Howe et al., "A Single Recombinant Plasmid Expressing Two Major Outer Surface Proteins of the Lyme Disease Spirochete", Sicence, vol. 227, p. 645 (Fe. 1985).
Barbour et al., "Heterogeneity of Major Proteins in Lyme Disease Borreliae: A Molecular Analysis of North American and European Isolates", J. Infectious Diseases, vol. 152, No. 3, p. 478, Sep. 1985.
Howe et al., "Organization of Genes Encoding Two Outer Membrane Proteins of the Lyme Disease Agent *Borrelia burgdorferi* within a Single Transcriptional Unit", Infection and Immunity, Oct. 1986, p. 207.
Bergstrom et al., "Molecular Analysis of linear Plasmid–encoded major surface proteins, OspA and OspB, of the Lyme Disease spirochaete *Borrelia burgdorferi*", Molecular Microbiology, (1989), 3(4), 479–486.
Lane et al., "Antigenic Characteristis of *Borrelia burg-*
(List continued on next page.)

Primary Examiner—Hazel F. Sidberry
Attorney, Agent, or Firm—Felfe & Lynch

[57] ABSTRACT

The present invention provides a vaccine against Lyme disease, wherein it contains one or more monoclonal antibodies which are specific for the 31 kD antigen (OspA) or the 34 kD antigen (OspB) of *Borrelia burgdorferi*.

The present invention also provides a process for obtaining this vaccine, as well as new monoclonal antibodies and antigens.

1 Claim, 2 Drawing Sheets

FOREIGN PATENT DOCUMENTS

WO9304157 3/1993 WIPO.
WO9307897 4/1993 WIPO ............................ A61K 39/04
WO9308299 4/1993 WIPO ............................ C12P 21/06

OTHER PUBLICATIONS

*dorferi* isolates from Ixodid Ticks in California", J. Clinical Microbiology, Oct. 1989, pp. 2344–2349.

Wallich et al., "Cloning and sequencing of the gene encoding the outer surface protein A (OspA) of a European *Borrelia burgdorferi* isolate", Nucleic Acids Research, Nov. 1989.

Schaible et al, Infection and Immunity, "Demonstration of Antigen–Specific T Cells and Histopathological Alterations in Mice Experimentally Inoculated with *Borrelia burgdorferi*", Jan. 1989, pp. 41–47.

Schaible et al., "Monoclonal Antibodies specific for the outer surface protein A (OspA) of *Borrelia burgdorferi* prevent *Lyme borreliosis* in severe combined immunodeficiency (scid) mice", PNAS, vol. 87, pp. 3768–3772, May 1990.

Fikrig et al., "Protection of Mice Against the Lyme Disease Agent by Immunizing with Recombinant OspA", Science, Oct. 1990, p., 553.

Simon et al., "A mouse model for *Borrelia burgdorfer infection: approach to a vaccine against Lyme disease*", *Immunology Today*, vol. 12, No. 1 1991, p. 11.

Fig.1

DNA sequence with derived amino acid sequence of the 31 kDa antigen (OspA) from B.burgdorferi ZS7

```
atgaaaaaatatttattgggaataggtctaatattagccttaatagcatgtaagcaaaat
 M  K  K  Y  L  L  G  I  G  L  I  L  A  L  I  A  C  K  Q  N gttagcagccttgacgagaaaaacagcgtttcagtagatttgcctggtgaaatgaacgtt
 V  S  S  L  D  E  K  N  S  V  S  V  D  L  P  G  E  M  N  V cttgtaagcaaagaaaaaaacaaagacggcaagtacgatctaattgcaacagtagacaag
 L  V  S  K  E  K  N  K  D  G  K  Y  D  L  I  A  T  V  D  K cttgagcttaaaggaacttctgataaaaacaatggatctggagtacttgaaggcgtaaaa
 L  E  L  K  G  T  S  D  K  N  N  G  S  G  V  L  E  G  V  K gctgacaaaagtaaagtaaaattaacaatttctgacgatctaggtcaaaccacacttgaa
 A  D  K  S  K  V  K  L  T  I  S  D  D  L  G  Q  T  T  L  E gttttcaaagaagatggcaaaacactagtatcaaaaaaagtaacttccaaagacaagtca
 V  F  K  E  D  G  K  T  L  V  S  K  K  V  T  S  K  D  K  S tcaacagaagaaaaattcaatgaaaaaggtgaagtatctgaaaaaataataacaagagca
 S  T  E  E  K  F  N  E  K  G  E  V  S  E  K  I  I  T  R  A gacggaaccagacttgaatacacagaaattaaaagcgatggatctggaaaagctaaagag
 D  G  T  R  L  E  Y  T  E  I  K  S  D  G  S  G  K  A  K  E gttttaaaaagctatgttcttgaaggaactttaactgctgaaaaaacaacattggtggtt
 V  L  K  S  Y  V  L  E  G  T  L  T  A  E  K  T  T  L  V  V aaagaaggaactgttactttaagcaaaaatatttcaaaatctggggaagtttcagttgaa
 K  E  G  T  V  T  L  S  K  N  I  S  K  S  G  E  V  S  V  E cttaatgacactgacagtagtgctgctactaaaaaaactgcagcttggaattcaggcact
 L  N  D  T  D  S  S  A  A  T  K  K  T  A  A  W  N  S  G  T tcaactttaacaattactgtaaacagtaaaaaaactaaagaccttgtgtttacaaaagaa
 S  T  L  T  I  T  V  N  S  K  K  T  K  D  L  V  F  T  K  E aacacaattacagtacaacaatacgactcaaatggcaccaaattagaggggtcagcagtt
 N  T  I  T  V  Q  Q  Y  D  S  N  G  T  K  L  E  G  S  A  V gaaattacaaaacttgatgaaattaaaaacgctttaaaataa
 E  I  T  K  L  D  E  I  K  N  A  L  K  *
```

Fig. 2

Immunological characterisation of the recombinant protein rZS7/31-2

BORRELIA BURGDORFERI STRAIN 257

This is a divisional of Ser. No. 07/937,054 filed Aug. 26, 1992 which in turn is a Divisional of Ser. No. 07/585,310, filed Sep. 19, 1990, now U.S. Pat. No. 5,178,859.

The present invention is concerned with a vaccine against Lyme disease, with a process for obtaining said vaccine, with new monoclonal antibodies, with new antigens and with new recombinant DNA's and vectors.

Lyme borreliosis is the most common infectious disease transmitted by ticks in the temperate regions. It is caused by the spirochete Borrelia burgdorferi which is transmitted to humans in particular by ticks of the genus Ixodes. The disease is a chronic, progressive infection which attacks many organs, such as the skin, the central and peripheral nervous system, the heart, the liver, the kidneys and musculoskeletal system. Since a reliable treatment of this disease by therapy with antibiotics is difficult, at the moment great efforts are being made to investigate the pathogen itself and the immune response of the host to infection with Borrelia burgdorferi. In the case of persons afflicted by Lyme disease, there is admittedly ascertained a high titre of antibodies against Borrelia burgdorferi which, however, do not provide any protection against the infection. It is assumed that the pathogen passes over very quickly from the blood circulation into the tissues and can there no longer be directly reached by the immune system. This would mean that a protection by antibodies is only possible immediately after commencement of the infection, i.e. as long as the pathogen is still present in the blood circulation.

The fact that a natural infection with Borrelia burgdorferi has been found in various kinds of animals has led to attempts to establish laboratory models for Lyme disease. This also took place with limited success. Thus, in the case of experiments which had the object of inducing in mice a specific immune response for Borrelia burgdorferi, it was found that the infection of inbred mouse strains with a prolonged cultured isolate of Borrelia burgdorferi led to moderate but significant pathomorphological changes in various organs, such as the brain, the heart, the lungs and the kidneys, which were comparable to those which are to be observed in patients with Lyme disease (see Schaible et al., Infect. Immun., 1, 41/1988). The development of a serious aspect of the disease in animals was presumably prevented either by the immune defence of the host and/or by the reduced virulence of spirochetes cultured in vitro for a comparatively long period of time (see Johnson et al., J. Clin. Microbiol., 20, 747/1984; Schwan et al., Infect. and Immun., 56, 1837/1988).

It is the object of the present invention to provide an effective vaccine against Lyme disease. However, for this purpose, it is first necessary to develop an appropriate animal laboratory mode. It is now suggested that a mouse strain without functionable T- and B-cells, the so-called scid mouse (see Bosma et al., Nature, 10, 52/1983) can serve as experimental animal since scid mice, in the case of infection with a pathogenic Borrelia burgdorferi isolate, develop a multi-systemic disease, namely, mainly polyarthritis and carditis. By means of this animal model, it is possible for the first time to test the action of vaccines against Lyme disease.

One subject of the present invention is a passive vaccine against Lyme disease which contains one or more specific monoclonal antibodies for the 31 kD antigen (OspA) and/or the 34 kD antigen (OspB) of Borrelia burgdorferi and especially OspA and/or OspB of Borrelia burgdorferi of the strain B31 (ATCC 35210) and/or ZS7 (DSM 5527). A vaccine is preferred which contains one of the antibodies of the class IgG according to the present invention and especially preferably of the subclass IgG2b or IgG1. Surprisingly, in contradistinction to the administration of another antibody, for example against the 41 kD surface antigen of Borrelia burgdorferi (flagellin), the administration of the antibody according to the present invention has the result, in the case of immune-deficient experimental animals and preferably of scid mice which have been infected with viable pathogenic Borrelia burgdorferi and preferably with Borrelia burgdorferi ZS7, that the development of arthritis, carditis and hepatitis is completely or at least substantially prevented.

The vaccine according to the present invention with the antibody as active material can possibly also contain conventional carrier, filling and adjuvant materials.

Furthermore, the present invention provides a process for obtaining a passive vaccine against Lyme disease from lymphocytes or spleen cells of an experimental animal, preferably of a mouse, which has been immunised with Borrelia burgdorferi organisms or parts thereof, preferably with complete Borrelia burgdorferi B31 and/or ZS7 organisms, in which, from the lymphocytes or spleen cells of the immunised animals, there is obtained by cell fusion, a hybridoma which produces a monoclonal antibody according to the present invention.

Thus, a subject of the present invention is also a hybridoma cell line (ECACC 89091302) which produces an antibody LA-2 against OspA (IgG2b) according to the present invention. Furthermore, the subject of the present invention is also the hybridoma cell line ECACC 90050406 producing the antibody LA-26.1 against OspA (IgG1), as well as the hybridoma cell lines ECACC 90050405 and ECACC 90050407 producing antibodies LA-25.1 and LA-27.1, respectively, against OspB (IgG2b and IgG1, respectively).

Furthermore, the present invention provides the pathogenic Borrelia burgdorferi strain ZS7 (DSM 5527).

In addition, the subject of the present invention is an antigen which immune-reacts with a monoclonal antibody according to the present invention. By this is to be understood an antigen which contains the whole amino acid sequence of OspA or OspB or also only an immunogenically-acting part sequence (immunogenic epitope) of OspA or OspB, respectively. Potentially immunogenic epitopes of these proteins can be determined without difficulty by a structural analysis of the OspA protein, for example a Chou-Fasman analysis, and then tested experimentally for their effectiveness.

Yet another subject of the present invention is also, in particular, a recombinant antigen which immune-reacts with the antibody according to the present invention in which the DNA sequence coding for the antigen is present on a recombinant vector, preferably a prokaryotic vector, which is suitable for the protein expression.

Figure 1:
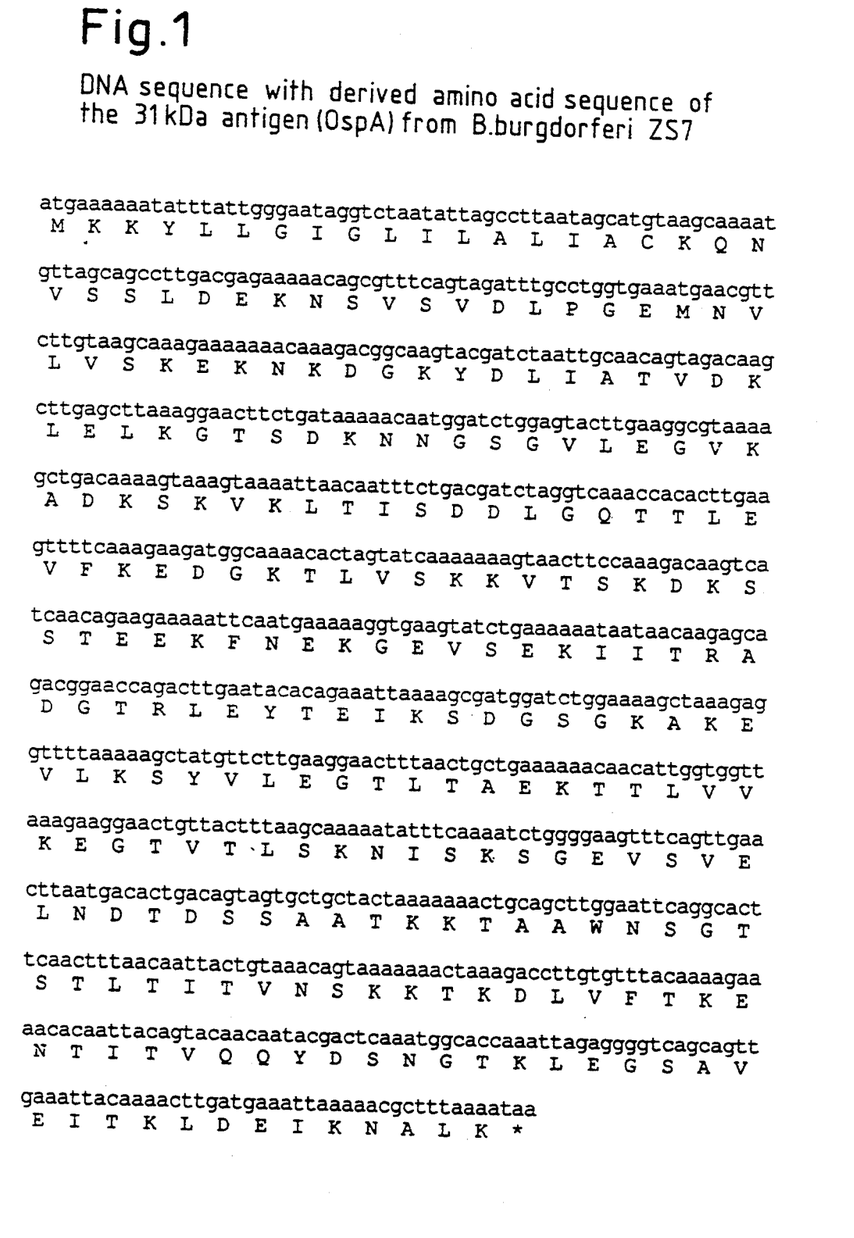
FIG. 1 shows the DNA and amino acid sequence of the 31 kD antigen (OspA) from Borrelia burgdorferi strain ZS7 and FIG. 2 shows the immunological characterisation of the recombinant protein rZS7/31-2.

In particular, a subject of the present invention is an antigen from Borrelia burgdorferi ZS7 which specifically immune-reacts with the antibody according to the present invention and which contains the amino acid sequence shown in FIG. 1 of the accompanying drawings or an immunogenic epitope of this sequence. Consequently, the present invention also concerns a recombinant DNA which contains (1) the sequence shown in FIG. 1, (2) a nucleic acid sequence corresponding to it in the scope of the degeneration of the genetic code or (3) one hybridising under stringent conditions with a sequence from (1) and/or (2), which sequence codes for the 31 kD antigen of Borrelia burgdorferi strain ZS7 or an immunogenic epitope thereof. The term stringent hybridising conditions is thereby to be understood as in Maniatis et al., Molecular Cloning, A Laboratory Manual (1982), Cold Spring Harbor Laboratory, New York.

Especially preferred is an antigen according to the present invention which is a recombinant non-fusion protein or β-galactosidase fusion protein.

Furthermore, the present invention is concerned with a recombinant vector which contains one or more copies of a recombinant DNA according to the present invention. The vector according to the present invention can be a prokaryotic and/or eukaryotic vector but is preferably a prokaryotic vector. The recombinant vector can be present extrachromosomally in the host cell (for example plasmid) or it can also be integrated in the genome of the host cell (for example bacteriophage lambda). The vector according to the present invention is preferably a plasmid, the recombinant vector pZS-7/31-2 (DSM 5528) being especially preferred.

The present invention also provides a process for obtaining antigens according to the present invention by investigation of a Borrelia burgdorferi gene bank with one or more antibodies according to the present invention in which the clones are isolated which show a positive immune reaction with the antibodies used.

Since the antigen according to the present invention itself also can be used for active immunisation, i.e. for the induction of antibody formation in the organism, the present invention also provides an active vaccine against Lyme disease which, as active material, contains an antigen according to the present invention, optionally together with conventional carrier, filling and adjuvant materials. A preferred embodiment is when the antigen according to the present invention is obtained gene-technologically.

Indeed, it could be shown that the administration of native or recombinant OspA to normal mice induces the formation of protective antibodies which, after passive transfer into scid mice, protect these against Lyme borreliosis. In particular, it is found that recombinant OspA induces a protective immune response comparable with native OspA and, therefore, represents a highly promising condidate for a vaccine against Lyme borreliosis in humans.

The present invention also provides a process for obtaining a passive vaccine against Lyme disease in which experimental animals, preferably mice, are immunised with an antigen according to the present invention and protective, polyclonal or monoclonal antibodies are obtained in the usual way from the immunised experimental animals.

Finally, the present invention also provides a process for the isolation and reculturing of pathogenic Borrelia burgdorferi organisms, wherein, from immune-deficient experimental animals, preferably mice, which have previously been infected with the pathogen, there is obtained the pathogen, whereby the pathogeneity of the pathogen is retained. Especially preferred is a process in which pathogenic Borrelia burgdorferi strain ZS7 (DSM 5527) organisms are obtained from the blood and/or joints of infected scid mice.

The following examples are given for the purpose of illustrating the present, reference being made to the accompanying drawings, in which.

EXAMPLE 1

Induction of Arthritis, Carditis and Hepatitis in Scid Mice by Infection with Borrelia burgdorferi Strain ZS7

Treatment of the Mice with Borrelia burgdorferi

Adult mice of the strains C.B-17 scid (homozygous for the scid mutation) and C.B-17 were injected subcutaneously into the root of the tail with $1 \times 10^5$, $5 \times 10^5$, $1 \times 10^6$ or $1 \times 10^8$ viable or killed (ultra-violet irradiation) Borrelia burgdorferi organisms.

Isolation of Borrelia burgdorferi from Ticks and Mice

The investigations were carried out with the Borrelia burgdorferi strain B31 (ATCC 35210), already cultured for a long time, and the fresh isolate Borrelia burgdorferi strain ZS7 (DSM 5527) which had been isolated from a female Ixodes rizinus tick. All Borrelia burgdorferi strains were cultured in modified Kelly' medium (see Barbour et al., Switzerland Curr. Microbiol., 8/123/1983). Borrelia burgdorferi organisms which had been obtained from the midgut of ticks sterilised with ethanol or from the blood of infected mice were initially cultured in Kelly's medium with the addition of 8 μg./ml. of kanamycin and 230 μg./ml. fluorouracil (see Johnson et al., J. Clin. Microbiol., 1, 81/1984).

Serological Tests

The detection of Borrelia burgdorferi-specific antibodies was carried out in a conventional ELISA process (see Justus et al., Wehrmed. Mschr., 32, 263/1988). The standard curve for the content of immuno globulin (Ig) was obtained by coating a dish with anti-mouse Ig (1:500 dilution of the serum solution of Paesel, Frankfurt, Federal Republic of Germany) and titration of the total mouse IgG or IgM content (Calbiochem, La Jolla, U.S.A.). Total serum IgM and IgG were measured in a similar manner. The concentration of Borrelia burgdorferi-specific IgM or IgG antibodies is given in μg. Ig/ml. or serum.

Immunofluorescence and Giemsa Staining

50 μl. of blood were pipetted into a haemocrit test-tube (Becton and Dickinson, Heidelberg, Federal Republic of Germany) and centrifuged at 5000 g in a haemocrit centrifuge (ECCO, Federal Republic of Germany). The test tubes were cut up on the interphase between serum and erythrocytes and 5 μl. of the serum were applied to microscope slides (Superior, Bad Mergentheim, Federal Republic of Germany). The microscope slides loaded with the serum samples were dried in the air and fixed in 100% ethanol for 1 minute at −20° C. After incubation for 1 hour with rabbit anti-Borrelia burgdorferi hyperimmune serum (1:100 dilution) at ambient temperature, with microscope slides were washed five times in PBS and then stained for 1 hour with FITC-conjugated goat anti-rabbit antiserum (1:20 dilution, Jackson Lab., West Grove, U.S.A.). The microscope slides were washed and embedded in Kaiser's glycerol gelatine (Merck, Darmstadt, Federal Republic of Germany) and immediately investigated by fluorescence microscopy. Untreated blood droplets were dried in the air, fixed in methanol, stained with Giemsa's stain (0.1%, Merck, Darmstadt, Federal Republic of Germany), decolorised in PBS and embedded in Entellan (Merck, Darmstadt, Federal Republic of Germany).

Histological Preparations and Staining Processes

Various internal organs (brain, heart, lungs, liver, kidneys, spleen and joints) were removed from mice previously infected with *Borrelia burgdorferi* at different times after the infection and stored either in liquid nitrogen for the preparation of frozen sections or in 5% formaldehyde (in PBS) for embedding in paraffin or methacrylate. Sections of 4 to 7 μm. thickness were prepared, stained with haemotoxylin-eosin and embedded in Entellan (Merck, Darmstadt, Federal Republic of Germany). The immunohistology was carried out with the use of streptavidin-biotin-peroxidase system (see Kramer et al., Eur. J. Immunol., 19, 151/1989).

Table 1 shows that *Borrelia burgdorferi* organisms of arthritis (reddening and swelling of both tibiotarsal joints), which increased in the course of time. On the other hand, no symptoms of arthritis were found in scid mice which had been infected either with ultra-violet irradiated *Borrelia burgdorferi* organisms (ZS7) or with viable *Borrelia burgdorferi* organisms (B31) in C.B-17 control mice which had been infected with viable *Borrelia burgdorferi* ZS7 organisms. Arthritic joint changes were also detected histopathologically in scid mice which had been infected with viable *Borrelia burgdorferi* organisms (ZS7 ) (see Table 1). Severe joint damages were ascertained, characterised by the presence of hyperplastically inflamed synovial lining cells, combined with erosion and destruction of cartilaginous tissue and/or bone. Furthermore, there was ascertained pancarditis with infiltration of mononuclear cells in the endocardium, myocardium and pericardium. There was also ascertained a progressive inflammation of the liver in which there was observed an infiltration of mononuclear cells, which was limited to the portal artery region and the central veins, granulomatous reactions and, finally, the appearance of liver fibrosis. In addition, smaller damage in the kidneys, the lungs, the brain and the striated musculature were ascertained.

TABLE 1

Infection of C.B-17 scid mice and C.B-17 control mice with *Borrelia burgdorferi*; reisolation of Spirochaetes from the tissue; antibody titre and formation of arthritis

| mouse strain | *B. burgdorferi* strain | *B. burgdorferi* number in infection | days after infection | *B. burgdorferi* detection in the blood+ | isolation | arthritis clinical | arthritis histo-pathological | antibody (μg./ml)°° total Ig μ | total Ig γ | specific Ig μ | specific Ig γ |
|---|---|---|---|---|---|---|---|---|---|---|---|
| C.B-17 | ZS7 | $5 \times 10^5$ | 7 | + | — | — | — | — | 20 | — | — |
|  |  |  | 36 | + | +B | + | + | — | 21 | — | — |
|  |  |  | 49 | + | +B | + | + | — | 26 | — | — |
|  |  |  | 59 | + | +B | + | + | — | 396 | — | — |
|  | ZS7 | $1 \times 10^8$ | 7 | + | — | + | + | — | 108 | — | — |
|  |  |  | 23 | + | +B | + | + | — | 54 | — | — |
|  | ZS7 | $1 \times 10^8$ | 22 | + | — | + | + | — | 41 | — | — |
|  |  |  | 29 | + | +J | + | + | — | — | — | — |
|  |  |  | 87 | + | +B/J | + | + | — | — | — | — |
|  | ZS7 | $1 \times 10^5$ | — | nd | nd | + | nd | nd | nd | nd | nd |
|  |  | $1 \times 10^6$ | — | nd | nd | + | nd | nd | nd | nd | nd |
|  |  | $1 \times 10^8$ | 16 | + | + | + | + | — | — | — | — |
|  | ZS7uv$_{tr}$ | $1 \times 10^8$ | 16 | — | — | — | — | — | — | — | — |
|  | B31 | $1 \times 10^8$ | 22 | + | — | — | — | 26 | 37 | — | — |
|  |  |  | 29 | + | — | — | — | — | — | — | — |
|  | — |  | 22 | — | — | — | — | — | 47 | — | — |
|  | — |  | 29 | — | — | — | — | 54 | 364 | — | — |
| C.B-17 (n = 7) | ZS7 | $1 \times 10^8$ | 16 | — | — | — | — | 2.515 | 5.963 | 438 | 56 |
|  |  |  | 24 | — | — | — | — | 2.145 | 6.374 | 506 | 94 |
|  | — | — | — | — | — | — | — | 304 | 3.804 | — | — |
|  | — | — | — | — | — | — | — | 216 | 1.952 | — | — | the isolates ZS7 and B31 were detected during the whole of the experimental period in the blood of scid mice which had previously been inoculated with viable organisms. However, only spirochetes of strain ZS7 but not of strain B31 could be recultured in vitro. In the case of comparison of the recultured organisms with the primary *Borrelia burgdorferi* ZS7 isolate, no changes in the protein content or in the plasmid profile could be ascertained. No or only extremely small titres of irrelevant antibodies were detected in scid mice infected with *Borrelia burgdorferi* during the entire period of observation. No IgM or IgG antibodies specific for *Borrelia burgdorferi* could be found in these animals (see Table 1). On the other hand, all C.B-17 control mice, which had been infected with *Borrelia burgdorferi*, expressed large amounts of total Ig and increased titres of IgM and IgG antibodies specific for *Borrelia burgdorferi*. Between 7 and 20 days after infection with *Borrelia burgdorferi*, scid mice showed the first clinical symptoms of + = by Giemsa staining or immunofluorescence
+ + = isolation from blood (B), joint (J)
o+ = reddening and swelling of the tibiotarsal joint
oo— = <7.5 μg./ml. serum

EXAMPLE 2

Action of a Monoclonal Antibody Specific for the *Borrelia burgdorferi* 31 kD Antigen on the Course of Lyme Borreliosis in Scid Mice Preparation of the Monoclonal Antibody In the case of immunisation of a mouse which has an intact immune system with *Borrelia burgdorferi* organisms, polyclonal antibodies are expressed which are specific for *Borrelia burgdorferi* (see Table 1).

Ten week old female mice of the inbred strain BALB/c were immunised with Borrelia organism (*Borrelia burgdorferi*, strain B31; ATCC 35210) homogenised by sonication.

Immunisation protocol:

day 0: 200 µg. Borrelia antigen in complete Freund's adjuvant subcutaneously day 21, 35, 49, 63: challenge with 100 µg. Borrelia antigen in phosphate-buffered saline (PBS) intraperitoneally day 66: removal of the spleen and preparation of a suspension of individual cells The immune spleen cells were fusioned with the Ag8-PA1 myeloma cell line by standard methods with the use of polyethylene glycol (see J. H. Peters, H. Baumgarten, M. Schulze, "Monoklonale Antikörper", pub. Springer Verlag, Heidelberg).

The fusion products were seeded out into 96 well tissue culture plates. After 8 days, the cell culture supernatants were investigated for the presence of Borrelia burgdorferi-specific monoclonal antibodies with the help of a solid-phase ELISA (see J. H. Peters et al., loc. cit.).

The hybridoma cells from antibody-producing cultures were cloned according to the marginal dilution method. The culture supernatants of individual clones were subsequently again characterised in the solid-phase ELISA, as well as by Western blot analysis and by immunofluorescence investigation. The monoclonal antibody LA-2 of the subclass IgG2b is produced by a monoclonal hybridoma line and secreted and reacts in the Western blot with the 31 kDa structure (OspA) of all investigated Borrelia burgdorferi strains (inter alia the isolates ZS7 and B31) in the case of contact with Borrelia burgdorferi proteins separated electrophoretically via an SDS gel and transferred by means of Western blot to a membrane. The monoclonal antibodies LA-26.1 (anti-OspA IgG1), LA 25.1 (anti-OspB (34 kDa antigen); IgG2b) and LA 27.1 (anti-OspB (34 kDa antigen) IgG1) were prepared and characterised in an analogous manner.

Infection of Mice with Borrelia burgdorferi ZS7

C.B-17 scid mice were infected subcutaneously in the root of the tail with $1 \times 10^8$ viable Borrelia burgdorferi organisms (ZS7).

Treatment of the Mice with Antisera

The infected scid mice were treated twice a week with various antisera. One group was treated with NMS (normal mouse serum), the second group with IMS (immune mouse serum) and the third group with the monoclonal antibody LA-2 (against the 31 kD antigen of Borrelia bergdorferi). The dosage of the administered antisera was 100 µl. or 100 µg. in the first week in the case of LA-2, 200 µl. or 200 µg. in the second week in the case of LA-2 and 300 µl. or 300 µg. in the third week in the case of LA-2.

The following Table 2 shows that scid mice, untreated or treated with NMS, develop clinical and histopathological indications of arthritis or carditis and hepatitis after 12 days. On the other hand, the administration of the monoclonal antibody LA-2 brings about a distinct reduction of the symptoms in the case of scid mice. Clinically, there were only ascertained slight reddenings of the joints and histopathologically only marginal changes. Mice treated with IMS showed no clinical findings of arthritis.

A detection of Borrelia burgdorferi organisms by in vitro culturing only succeeded in the case of mice which were either untreated or treated with NMS. In the case of mice treated with LA-2 or IMS, Borrelia burgdorferi organisms could not be detected (Table 2).

TABLE 2

| mouse strain C.B-17 scid | treatment with anti-serum | arthritis (after 12 days) | | carditis/ hepatitis | B. burgdorferi detection (culture) |
|---|---|---|---|---|---|
| | | clinical | histopathological | histopathological | |
| n = 3 | — | + | + | + | + |
| n = 3 | NMS | + | + | + | + |
| n = 2 | IMS | — | — | — | — |
| n = 3 | LA-2 | —° | —°° | — | — |

° = slight reddening of the joint
°° = only marginal change

EXAMPLE 3

Expression Cloning of the 31 kD Antigen (OspA) of Borrelia burgdorferi ZS7

High molecular weight DNA from the Borrelia burgdorferi strain ZS7 was purified after culturing in modified Kelly's medium. The spriochetes were pelleted by centrifuging at 10,000 g and washed three times with PBS buffer. The dry pellet was resuspended in 10 ml. TE (10 mmole/liter Tris, 1 mmole/liter EDTA, pH 7.4), treated with lysozyme (5 mg./ml.) for 15 minutes at 30° C. and the DNA released by the addition of 1 ml. 20% SDS. After the addition of 1.5 ml. sodium chloride solution (5 mole/liter), the solution was extracted with an equal volume of phenol, followed by an extraction with chloroform. The DNA was then precipitated by the addition of 2 volumes of absolute ethanol and incubation at −20° C. overnight. After centrifugation, the pellet was dissolved in 0.5 ml. TE and incubated with DNAse-free RNAse A (20 µg./ml.) for 45 minutes at 55° C., followed by treatment for 1 hour with proteinase K (0.1 µg./ml.) at 37° C. The solution was adjusted to 0.3 mole/liter sodium acetate and extracted with phenol-chloroform as described above. After precipitation with ethanol, the DNA was dissolved in TE.

Preparation of the Gene Bank

High molecular weight DNA was randomly sheared by sonication for 3 seconds. T4-DNA polymerase (30 minutes at 37° C.) and Klenow enzyme (5 minutes at 20° C.) were used in order to fill in the single stranded ends of the generated DNA fragments. Blunt ended DNA was ligated into the BamHI site of an expression vector pUEX1 by using an adaptor cloning strategy (see Bresan and Stanley, Nucl. Acid Res., 1987, p. 1056). After size selection by molecular sieve chromatography over Sephacryl S-1000 and transformation of competent host cells Escherichia coli (MC 1061), the percentage of recombinant clones was determined as follows: randomly selected colonies were picked and cultured to saturation in 2 ml. of selection medium (LB with 25 µg./ml. of ampicillin). The plasmid DNA was isolated according to the usual alkaline lysis method and subsequently cleaved with BamHI. More than 50% of the analysed plasmids contained, were found to contain DNA-inserts with an average size of >1.5 kb.

Plating and Expression Screening of the Borrelia burgdorferi ZS7 Gene Bank

The cells were plated on 24×24 cm. plates at a density of 7000 colonies per plate and incubated overnight at 30° C. After transfer of the colonies to nitrocellulose filters (NC), the expression of β-galactosidase fusion proteins was induced by incubation for 2 hours at 42° C. The filters were transferred to a Whatman 3MM paper which had been treated with 5% SDS and incubated for about 25 minutes at 95° C. The proteins were then electro-blotted with the use of a conventional Western blotting apparatus. After DNAse treatment of the NC filters, immune-reactive clones were identified by an expression screening with the use of monoclonal antibodies. Non-specific binding sites on the NC filters were blocked by incubation for 4 hours with PBS containing 0.2% w/v of gelatine and 3 mmole/liter sodium azide at room temperature. Subsequently, the filters were incubated for 18 hours with continuous shaking with culture supernatants of the anti-31 kD monoclonal antibody LA-2. After extensive washing (PBS+1% v/v Triton X-100; PBS+0.5 mole/liter sodium chloride; PBS+1 mole/liter sodium chloride; each step 10 minutes), the filters were incubated with a 1:10000 dilution of a peroxidase-labelled F(ab)$_2$ preparation of rabbit-anti-mouse-IgG antibodies for 1.5 hours at room temperature with permanent shaking. The filters were again washed as described above and then incubated with diaminobenzidine as peroxidase substrate. Of $10^4$ recombinant clones, 20 clones reacted with the monoclonal antibody LA-2.

Sequence Analysis of the 31 kD Antigen (OspA)

The insert DNA of a recombinant *Escherichia coli* clone with positive antibody reaction with LA-2 was analysed and sequenced according to standard protocols (Maniatis et al., (1982) Molecular Cloning; A Laboratory Manual, Cold Spring Harbor Laboratory, Cold Spring Harbor). The DNA insert of this clone contained the OspA gene coding for the *Borrelia burgdorferi* 31 kD antigen in full length. The plasmid which contains the OspA gene was designated pZS-7/31-2 and was deposited according to the Budapest Convention at the DSM under the number DSM 5528.

The recombinant protein produced by this immune-positive clone was designated as rZS7/31-2. The DNA sequence of the OspA gene was determined. It is shown in FIG. 1 of the accompanying drawings, together with the amino acid sequence of the OspA protein deduced from the DNA sequence.

From FIG. 1, it can also be seen that the 31 kD antigen from *Borrelia burgdorferi* corresponds to a protein of 273 amino acids.

Preparation of Non-Fusion Proteins a) The clone which expresses the immune-reactive protein rZS7/31-2 was cultured overnight at 30° C. in 10 ml. LB with ampicillin. 1 ml. of the culture was introduced into the selection medium and cultured at 30° C. with good aeration up to saturation.

After cooling and centrifugation, the cells were washed in STE buffer (10 mmole/liter Tris, 100 mmole/liter sodium chloride, 1 mmole/liter EDTA, pH 8.0) and the pellet resuspended in 0.6 ml. of lysis buffer (25% sucrose, 50 mmole/liter Tris, pH 8.0). After the addition of 150 μl. of lysozyme (10 mg./ml.), the mixture was incubated for 15 minutes on ice, followed by a further incubation (15 minutes on ice) with 18 μl. DNAse 1 (10 mg./ml.) in the presence of 5 μl. of 1 mole/liter magnesium chloride. Finally, 250 μl. 4× detergent mixture (1% Triton X100, 0.5% deoxycholate, 0.1 mole/liter sodium chloride, 10 mmole/liter Tris, pH 7.4) were added, followed by an incubation on ice for 5 minutes. After centrifugation, the pellet was washed twice with buffer A (50 mmole/liter Tris, 50 mmole/liter sodium chloride, 1 mmole/liter EDTA, pH 8.0) and resuspended in 9 volumes of buffer A contained 8M urea and incubated for 1 hour at room temperature. The sample was diluted with 9 parts of buffer B (50 mmole/liter monopotassium dihydrogen phosphate/dipotassium monohydrogen phosphate, 50 mole/liter sodium chloride, 1 mmole/liter EDTA, pH 10.7) and stirred for 30 minutes at room temperature, the pH being maintained at 10.7 by the addition of potassium hydroxide solution. After adjustment of the pH of the solution to 7.0 by the addition of hydrochloric acid, the sample was dialysed overnight against buffer A at 4° C. and centrifuged for 10 minutes at 4° C. and 10,000 r.p.m. in an SS34 rotor. The supernatant, which contains the recombinant protein, was stored at −20° C.

b) Since the clone also secretes the immune-reactive protein rZS7/31-2 into the culture medium, a purification (affinity chromatography) directly from the culture supernatant was performed.

Preparation of Recombinant OspA (Non-Fusion) Protein and Purification by Affinity Chromatography The recombinant proteins were subsequently purified by affinity chromatography. For this purpose, purified monoclonal antibodies LA-2 were covalently bound to activated Sepharose CL 4B. The dialysed urea extract or the culture supernatant with the recombinant protein was adsorbed on mouse IgG-Sepharose CL 4B and subsequently passed over the LA-2-Sepharose CL 4B column. After intensive washing, the bound recombinant protein was eluted with 0.1 mole/liter glycine/hydrochloric acid—0.1 mole/liter sodium chloride, pH 2.5. The pH value of the collected fractions was immediately adjusted to neutral by the addition of 1/lo volume of 0.5 mole/liter dipotassium monohydrogen phosphate. The protein-containing fractions were concentrated and dialysed. The degree of purification was determined by SDS-polyacrylamide gel electrophoresis.

Immunological Characterisation of the Recombinant Protein rZS7/31-2

The recombinant protein rZS7/31-2 was investigated immunologically. For comparison, recombinant protein rB31/41-9 (*Borrelia burgdorferi* 41 kD surface antigen) was used.

Flat-bottomed microtitre plates were coated with urea extracts of the recombinant proteins rZS7/31-2 and rB31/41-9 or with a urea extract of the *Escherichia coli* strain MC 1061 used for the gene expression. Non-specific binding sites were blocked by incubation with 0.2 gelatine in phosphate-buffered sodium chloride solution.

Microtitre plates were incubated with the given monoclonal antibodies LA-2 (anti-31 kD, OspA), LA-1 (anti-41 kD, flagellin) or ACHT-2 (anti-$\alpha_1$-antichymotrypsin).

Bound monoclonal antibodies were detected via peroxidase-labelled, species-specific anti-mouse immuno-globulins. Bound peroxidase-labelled antibodies were quantified by using the peroxidase substrate o-phenylenediamine. The adsorption at 492 nm ($A_{492}$) was determined directly in the microtitre plates with the help of an automated plate photometer. The adsorption is proportional to the amount of bound monoclonal antibodies.

The monoclonal antibody LA-2 reacts in a specific manner with rZS7/31-2 but not with MC 1061 or rB31/41-9. For control reaction the monoclonal antibody LA-1 which is specific for rB31/41-9 is used. The monoclonal antibody ACHT-2 (negative control) does not show a significant reaction on any of the proteins.

Figure 2:
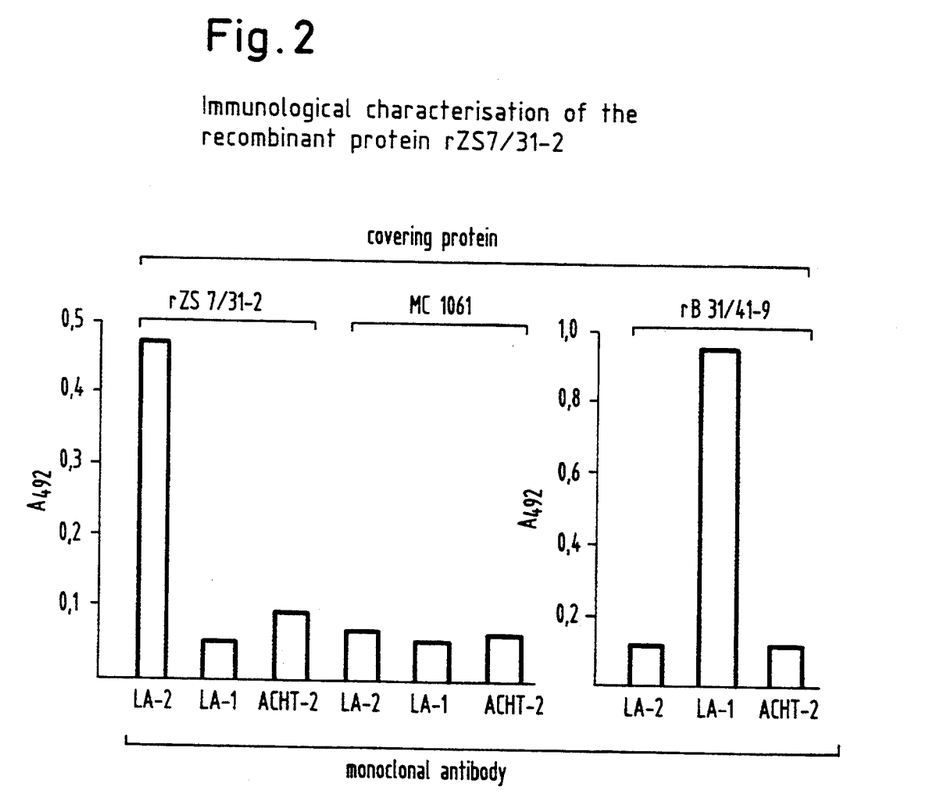

FIG. 2 of the accompanying drawings shows that the antigenic epitope recognized in a specific manner by the monoclonal antibody LA-2 is expressed on the recombinant protein rZS7/31-2 which was cloned from the genome of Borrelia burgdorferi ZS7.

EXAMPLE 4

Comparison of Antibodies Specific for the 31 kD (Ospa) or the 34 kD Antigen (OspB) and Antibodies Which are Specific for the 41 kD Antigen (Flagellin)

The monoclonal antibodies LA-2 and LA-26.1 recognize the 31 kD antigen OspA and are of the isotype IgG2b and IgG1, respectively. The monoclonal antibodies LA-25.1 and LA-27.1 recognize the 34 kD antigen OspB and are of the isotype IgG2B and IgG1, respectively. The monoclonal antibodies LA-10 and LA-21 are specific for the flagella-associated 41 kD periplasmatic protein (flagellin) of Borrelia burgdorferi and are of the isotype IgG2a and IgG1, respectively. All the above-mentioned antibodies were obtained according to the process described in Example 2. In this experiment, it is to be ascertained whether monoclonal antibodies against another Borrelia burgdorferi antigen in scid mice also confer protection against the clinical symptoms of lyme borreliosis.

The polyclonal anti-B31 immune serum (IMS) was taken from C57BL/6 mice 91 days after a subcutaneous inocculation with $1 \times 10^8$ Borrelia burgdorferi B31 organisms. The polyclonal anti-ZS7 IMS was taken from C57BL/6 mice 68 days after a subcutaneous inoculation with $1 \times 10^8$ Borrelia burgdorferi ZS7. Both sera contained 60 μg./ml. of specific antibodies, as was determined in an ELISA system (see Schaible et al., J. Exp. Med., 170, 1427–1432/1989). The normal mouse serum (NMS) was taken from non-infected C57BL/6 mice.

At the point of time of the inoculation and thereafter in 4 day intervals, the given antibodies, the IMS, the NMS or PBS buffer were passively transferred intraperitoneally into scid mice according to the following protocol:

day 0 and day 3: 100 μl.
day 7 and day 10: 200 μl.
day 13 and day 17: 300 μl.

Scid mice which had been treated either with anti-ZS7IMS, anti-B31IMS or with the monoclonal antibody LA-2 showed no visible clinical symptoms of arthritis, i.e. no reddening and swelling of tibiotarsel joints occurred during the 21 days of observation. Also, no symptoms of carditis and hepatitis were ascertained. Histopathological investigations showed no changes in the joints, the heart and the liver of scid mice which had been treated either with anti-ZS7-IMS, anti-B31 IMS or with the monoclonal antibody LA-2.

The other OspA-specific monoclonal antibodies LA-26.1 of the isotype IgG1, as well as the OspB-specific antibodies LA-25.1 and LA-27.1, were able to mitigate the clinical symptoms of arthritis, carditis and hepatitis. Slight pathological changes in the investigated organs were here shown.

In contrast, scid mice which had been treated either with PBS buffer, NMS or monoclonal antibodies against flagellin (LA-10 or LA-21) showed clinical signs of arthritis, the pathological changes typical for untreated scid mice (see the following Table 3). The severity of the symptoms in the last-mentioned animals increased with increasing period of time after the inoculation and did not weaken during the period of observation.

No spirochetes could be isolated from scid mice which had previously been treated either with anti-ZS7IMS or with the antibody LA-2. In contrast the detection of Spirochaetes by immunofluorescence and by culturing of blood from scid mouse was possible in those mice which had been treated with PBS buffer, NMS or the monoclonal antibodies LA-25.1, LA-26.1, LA-27.1, LA-10 or LA-21.

TABLE 3

| mouse strain C.B-17 scid (number of mice) | treatment with | IgG subtype | clinical arthritis | histopathology periarthritis/ arthritis | carditis | detection of B. burgdorferi (culturing and immunofluorsecence) |
|---|---|---|---|---|---|---|
| n = 8 | PBS (negative control) |  | + | + | + | + |
| n = 3 | NMS (negative control) |  | + | + | + | + |
| n = 3 | anti-B31 IMS |  | − | − | −+ | +° |
| n = 2 | anti-ZS7 IMS |  | − | − | −+ | − |
| n = 6 | LA-2 (OspA) | 2b | − | −+ | −+ | − |
| n = 3 | LA-10 (flagellin) | 2a | + | + | + | +° |
| n = 3 | LA-21 (flagellin) | 1 | + | + | +/− | + |
| n = 3 | LA-26.1 (OspA) | 1 | ± | ± | ± | +° |
| n = 3 | LA-25.1 (OspB) | 2b | ± | ± | ± | + |
| n = 3 | LA-27.1 (OspB) | 1 | ± | ± | ± | +° |

The degree of the histopathological change is indicated as follows: − none; −+ subclinical; +/− moderate; + severe.
° A detection of Borrelia burgdorferi by immunofluorescence was not possible in all investigated individuals.

EXAMPLE 5

Action of Antiserum from Mice Immunised with OspA on the Course of Lyme Borreliosis in Scid Mice In this experiment, it could be shown that an administration of native OspA (isolated from Borrelia burgdorferi strain ZS7) or of recombinant OspA (isolated from Escherichia coli bacteria which had been transformed with the recombinant plasmid pZS7/31-2 (DSM 5528)) into normal mice (mice strain C57BL/6) induced the formation of protective polyclonal antibodies. If these antibodies are administered to scid mice, there is brought about a protection against Lyme borreliosis. It is thereby ascertained that recombinant OspA induces a protective immune response comparable to that induced with native OspA. The results and the details of carrying out of this experiment are given in the following Table 4.

The obtaining of recombinant OspA is described in Example 3.

The obtaining of native OspA, as well as the immunising of mice with OspA, took place as follows:

Enrichment of Native 31 kDa OspA $3.2 \times 10^{10}$ spirochetes are stirred with a magnetic stirrer for 2 hours at 4° C. in 5 ml. of PBS/7.5 ml. n-butanol in the presence of protease inhibitor (5 mmole/-liter EDTA, 5 mmole/liter benzamidine and 0.5 mmole/liter PMSF). Thereafter, the mixture is centrifuged for 90 minutes at 10,000 r.p.m. in a Sorvall centrifuge (fixed-angle rotor). The aqueous phase which contains the surface proteins is removed and washed three times with chloroform. The protein content is determined via the extinction of 280 nm or with the BCA test.

In the silver gel or Western blot with anti-*Borrelia burgdorferi* rabbit serum, there was found for strain ZS7 a main band in the molecular weight range of 31 kDa, as well as weak bands at 20, 34, and 65–68 kDa. The butanol/water preparation of *Borellia burgdorferi* strain B31 gave a main band at 31 kDa, as well as weak bands at 20 and 34 kDa.

Immunisation of Mice with Native and Recombinant OspA

To C57BL/6 and C.B-17 mice were given three times subcutaneously into the root of the tail at an interval of 7 to 10 days 5 μg. (native OspA of strain B31) or 10 μg. (native OspA of strain ZS7, recombinant OspA of ZS7) in 100 μl. of adjuvant (ABM3; firm Sebak, Aidenback, Federal Republic of Germany). At the earliest 3 weeks after the last immunisation, serum could be taken for 3 to 4 months. The content of specific antibodies is determined in the ELISA system.

TABLĒ 4

Effect of *Borrelia burgdorferi*-Specific Monoclonal and Polyclonal Antibodies on Spirochaetosis and Development of Arthritis in Scid Mice Infected with *Borrelia burgdorferi*

| mouse strain C.B-17 scid (number of mice) | treatment with | development of arthritis after week(s) 1 | 2 | 3 | detection of *B. burgdorferi* |
|---|---|---|---|---|---|
| n = 6 | PBS (negative control) | ± | + | + | 6/6 |
| n = 6 | LA-2 | – | – | – | 0/3 |
| n = 2 | anti-OspA (native) IMS | – | – | – | 0/2 |
| n = 3 | anti-OspA (recomb,) IMS | – | – | – | 0/3 |

First antibody transfer i.p. (100 μl.) day 0 (day of the inoculation with *B. burgdorferi* strain ZS7, $1.10^8$ organisms, s.c. into the root of the tail).

Further antibody transfers day 4 (100 μl.), day 7 (200 μl.), day 11 (200 μl.), day 14 (300 μl.), day 18 (300 μl.),(i.p.)

We claim:

1. Isolated *Borrelia burgdorferi* strain ZS7, DSM 5527.

* * * * *